US005797867A

United States Patent [19]
Guerrera et al.

[11] Patent Number: 5,797,867
[45] Date of Patent: Aug. 25, 1998

[54] IONTOPHORETIC DRUG DELIVERY SYSTEM, INCLUDING METHOD FOR ACTIVATING SAME FOR ATTACHMENT TO PATIENT

[75] Inventors: Stephen K. Guerrera, Milford, Mass.; Michael I. Bernhard, Summit, N.J.

[73] Assignee: Becton Dickinson and Company, Franklin Lakes, N.J.

[21] Appl. No.: 722,816

[22] Filed: Sep. 27, 1996

[51] Int. Cl.⁶ .................................................. A61N 1/30
[52] U.S. Cl. .................................................. 604/20; 607/153
[58] Field of Search ........................ 604/20, 21; 607/153

[56] References Cited

U.S. PATENT DOCUMENTS

| 4,911,707 | 3/1990 | Heiber et al. |  |
|---|---|---|---|
| 4,917,676 | 4/1990 | Heiber et al. |  |
| 5,128,137 | 7/1992 | Müller et al. |  |
| 5,310,404 | 5/1994 | Gyory et al. | 604/20 |
| 5,423,739 | 6/1995 | Phipps et al. | 604/20 |
| 5,445,609 | 8/1995 | Lattin et al. | 604/20 |
| 5,662,925 | 9/1997 | Ebert et al. |  |

FOREIGN PATENT DOCUMENTS 0650197  12/1993  Australia ............................ 604/20

Primary Examiner—Mark Bockelman
Assistant Examiner—Ellen S. Tao
Attorney, Agent, or Firm—Allen W. Wark

[57] ABSTRACT

The user activated iontophoretic device of the present invention includes a disposable patch and a reusable controller. The patch contains an electrode assembly, an electrode reservoir and at least one drug reservoir. The patch is divided or otherwise separated into at least two portions, with one portion containing the electrode reservoir and the other containing the drug reservoir, which may include a medication in a dry form. The electrode reservoir and the drug reservoir are sealingly separated by a barrier, which can be manipulated to bring the reservoirs into fluid conducting contact with one another. A method of activating the device includes causing the two portions to rotate about a central axis relative to one another to manipulate the barrier and bring the reservoirs into fluid conducting contact with one another to at least partially hydrate one of the reservoirs. In this way, the device is suitable for use to deliver a drug which has limited stability in an aqueous solution.

20 Claims, 5 Drawing Sheets

5,797,867

1

IONTOPHORETIC DRUG DELIVERY SYSTEM, INCLUDING METHOD FOR ACTIVATING SAME FOR ATTACHMENT TO PATIENT

FIELD OF THE INVENTION

The present invention generally relates to iontophoretic drug delivery systems for delivering drugs, medicines, medicaments and the like to patients transdermally, i.e., through the skin, and more specifically relates to an iontophoretic drug delivery system and method for activating same for attachment to the skin of a patient.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. No. 4,820,263 (Spevak et al.), U.S. Pat. No. 4,927,408 (Haak et al.) and U.S. Pat. No. 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Direct current is applied between the two electrodes. Under the influence of the electric field present, the drug molecules migrate through the skin. As current flows between the two electrodes placed at spaced apart locations on the skin, the current path carries the drug with it.

However, with the increasing use of drugs, particularly peptides, peptidomimetics and the like, several disadvantages and limitations have been associated with the activation and use of such devices for delivering such drugs. Specifically, as a result of the need to store the drug in a dry form or otherwise isolate the drug from the aqueous solution in the electrolyte reservoir, such devices have become complicated as disclosed, for example, in U.S. Pat. No. 4,722,726 (Sanderson et al), U.S. Pat. No. 4,842,577 (Konno et al.), U.S. Pat. No. 4,911,707 (Heiber et al.), U.S. Pat. No. 4,917,676 (Heiber et al.), U.S. Pat. No. 5,087,242 (Pentelenz et al.), U.S. Pat. No. 5,158,537 (Haak et al.), U.S. Pat. No. 5,310,404 (Gyory et al.), and U.S. Pat. No. 5,385,543 (Haak et al.), the disclosures of which are hereby incorporated by reference in their entirety. In addition, such devices have been generally cumbersome to activate for attachment to the skin of the patient in doctor's offices, and in particular by outpatients having limited mobility or other impairments.

Thus, there has been a need for an iontophoretic drug delivery system which would eliminate the problems and limitations associated with the prior devices discussed above, most significant of the problems being associated with the effort necessary to activate the drug for attachment to the skin of the patient.

SUMMARY OF THE INVENTION

In contrast to the prior devices and systems discussed above, it has been found that a iontophoretic drug delivery system may be constructed in accordance with the present invention which can be easily used to activate the system and apply it to the skin of the patient. Users of such a system may include the patient as well as doctors, nurses and the like, including those having a physical impairment.

The user activated iontophoretic device of the present invention for use in delivering at least one medication through an applied area of a patient, such as the skin, mucus membrane and the like, includes a first portion and a second portion, the first portion including an electrode assembly and a electrode reservoir and the second portion including a drug reservoir, the electrode assembly including electrode means for driving a medication into the patient to be absorbed by the body of the patient, the drug reservoir containing a active compound to be delivered to the applied area of the patient, and barrier means for sealing the drug reservoir in the second portion, whereby the reservoirs are sealingly separated from one another with the active compound contained in the drug reservoir being isolated from the electrode reservoir in the first portion prior to activation so that upon alignment of the reservoirs and manipulation of the barrier means, the electrode reservoir and the drug reservoir are brought into fluid conducting contact with one another so that the drug is dissolved in an aqueous solution contained in the electrode reservoir.

In the preferred embodiment of the user activated iontophoretic device, upon activation, the active compound is dissolved at an interface of the two reservoirs, with the active compound in contact with the applied area of the patient prior to current being applied. Also, the active compound is initially in a dry form, separated from the electrode reservoir with the barrier means sealing the drug reservoir in the second portion or in a dry form and homogeneously distributed in a carrier material so that the active compound may be kept in a dry form, separated from the electrode reservoir, with the active compound may be selected from the group including cell adhesion molecules, GPIIb/IIIa receptor antagonists for the treatment of various thromboembolic disorders. In addition, the electrode reservoir includes an electrolyte such as an electrically conductive gel. The barrier means includes a foil seal having a tab, with the foil seal being adhered along the peripheral edge of the drug reservoir and the tab being adhered to the first portion so that movement of the first portion relative to the second portion manipulates the barrier means and brings the electrode reservoir and the drug reservoir into fluid conducting contact with one another, and the adhering force adhering the tab to the first portion is greater than the adhering force adhering the foil seal to the second portion. The first portion includes a compartment for at least containing the electrode reservoir and the second portion includes a compartment for containing the drug reservoir with the compartments sealingly separated by the barrier means so that the active compound is otherwise isolated from the electrode reservoir and the device may be activated by manipulating the barrier means to bring the electrode reservoir and the drug reservoir into fluid conducting contact with one another. Further, the user activated iontophoretic device also includes at least one spacer for separating the first portion and the second portion, with the spacer extending outwardly from either the first portion or the second portion and a corresponding recess formed in the other portion for accommodating the spacer.

The method of the present invention for iontophoretically delivering at least one medication through an applied area of a patient such as the skin, mucus membrane or the like includes the steps of releasably fastening a controller to a disposable patch, with the patch including an upper portion and a lower portion, rotating the upper portion about a central axis relative to the lower portion, manipulating a barrier means sealingly separating at least one electrode reservoir contained in the upper portion and a drug reservoir contained in the lower portion, with the drug reservoir containing an active compound to be delivered to the patient in a dry state, bringing the electrode reservoir of the upper portion into fluid conducting contact with the drug reservoir of the lower portion to at least partially hydrate one of the reservoirs and to form a combined reservoir, with the combined reservoir to be applied to an area of the patient to be treated, and causing current to flow through the device into the applied area to drive the medication into the body of the patient.

In the preferred embodiment of the method of iontophoretically delivering at least one medication, the step of bringing the two portions into contact with one another includes manipulating a seal at least partially releasably adhered to the lower portion Also, the method includes the step of removing a release liner from the lower portion to expose the reservoirs for application to the skin of the patient. In addition, the step of bring the electrode reservoir and the drug reservoir into contact with one another includes hydrating the drug reservoir or dissolving the drug contained in the drug reservoir into the electrode reservoir.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

DETAILED DESCRIPTION OF THE PREFERRED EMBODIMENT

The iontophoretic drug delivery system of the present invention is illustrated in FIGS. 1–5 and generally includes the designation 10. Referring to FIGS. 1–5, the device or system 10 of the present invention includes a patch 12 and a controller 14.

Figure 1A:
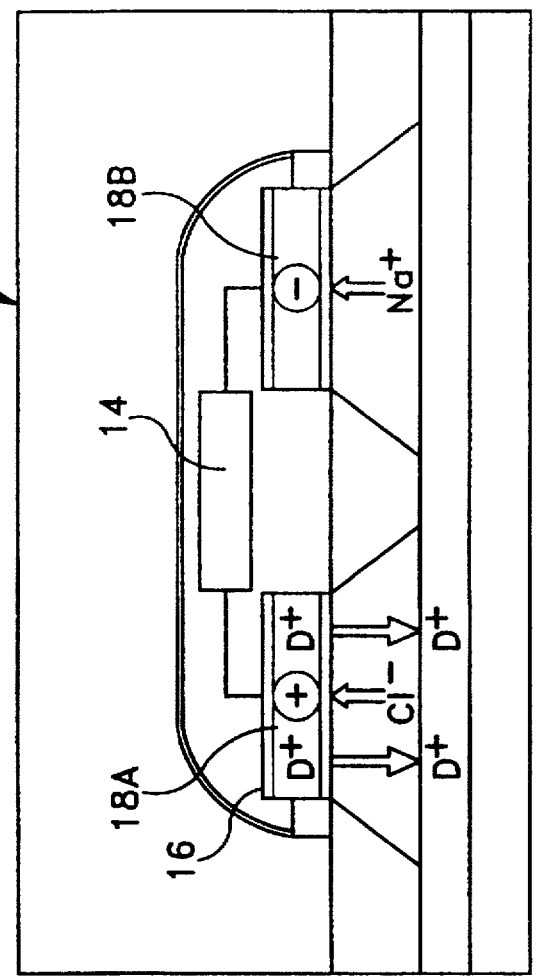
FIG. 1 is a schematic representation of the iontophoretic drug delivery system of the present invention attached to the arm of a user, with FIG. 1A being an enlarged, representation of the system.
Figure 2:
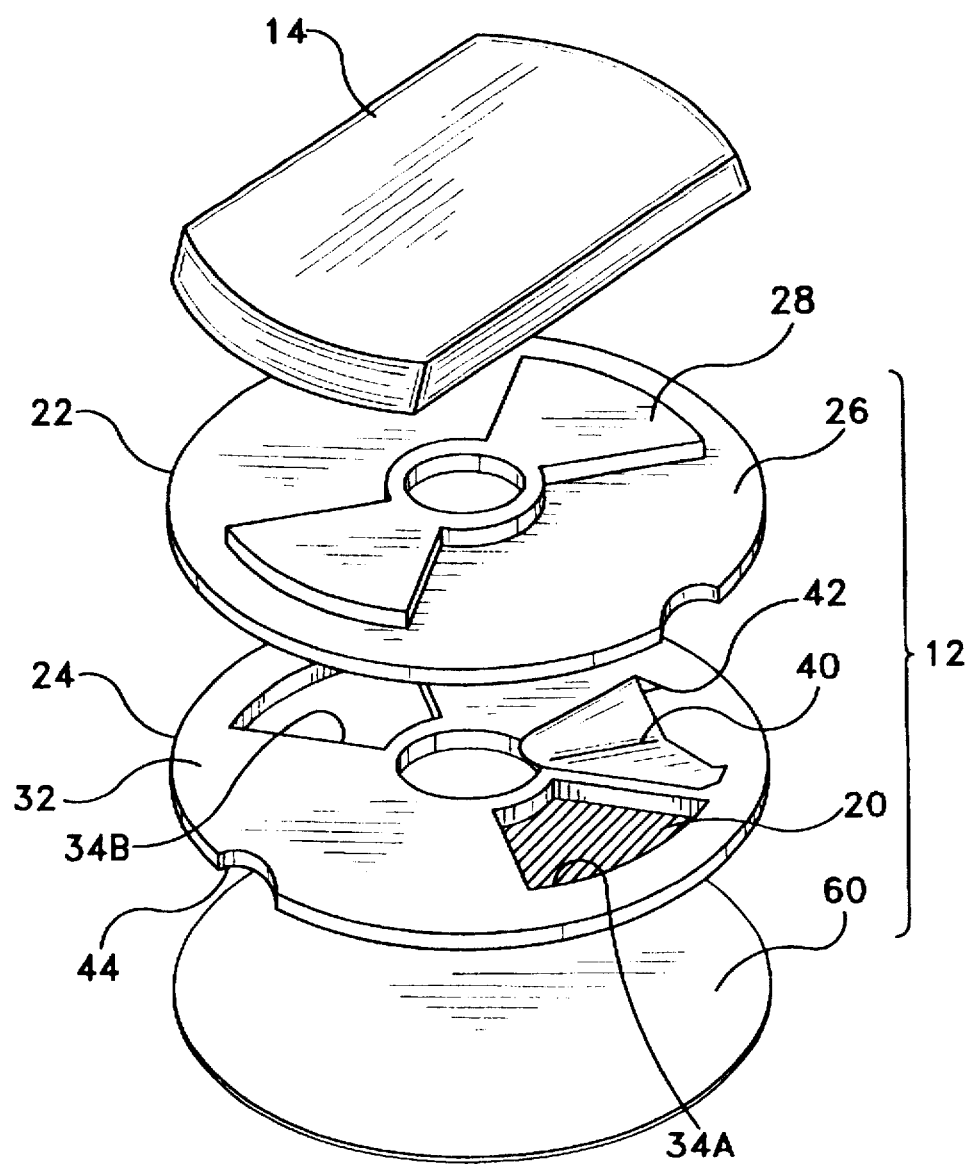
FIG. 2 is an exploded, perspective view of the iontophoretic drug delivery system of the present invention.

As illustrated in FIGS. 1A and 2, the patch 12 includes an electrode assembly 16, having at least two electrodes, corresponding electrode reservoirs 18A, 18B, and at least one drug reservoir 20, which are preferably held together by a suitable supporting structure divided or otherwise separated into two portions or members 22, 24, with one member 22 (upper) including the electrode assembly 16 and the electrode reservoirs 18A, 18B and the other member 24 (lower) including the drug reservoir 20 which holds the medication or drug, preferably in an ionized or ionizable form, to be delivered iontophoretically as disclosed in co-pending application Ser. No. 08/722,813, pending, entitled "USER ACTIVATED IONTOPHORETIC DEVICE AND METHOD FOR ACTIVATING SAME," the disclosure of which is hereby incorporated by reference in its entirety.

Referring to FIG. 2, the upper supporting member 22 includes a generally planar portion 26 and raised portion 28 having two compartments 30A, 30B for accommodating the electrode assembly, and in particular the electrode reservoirs 18A, 18B. The lower supporting member 24 includes a generally planar portion 32 and at least two openings 34A, 34B therein corresponding to the compartments 30A, 30B in the upper member 22. At least one of the openings 34A also forms a compartment for retaining the drug reservoir 20 therein.

Figure 4:
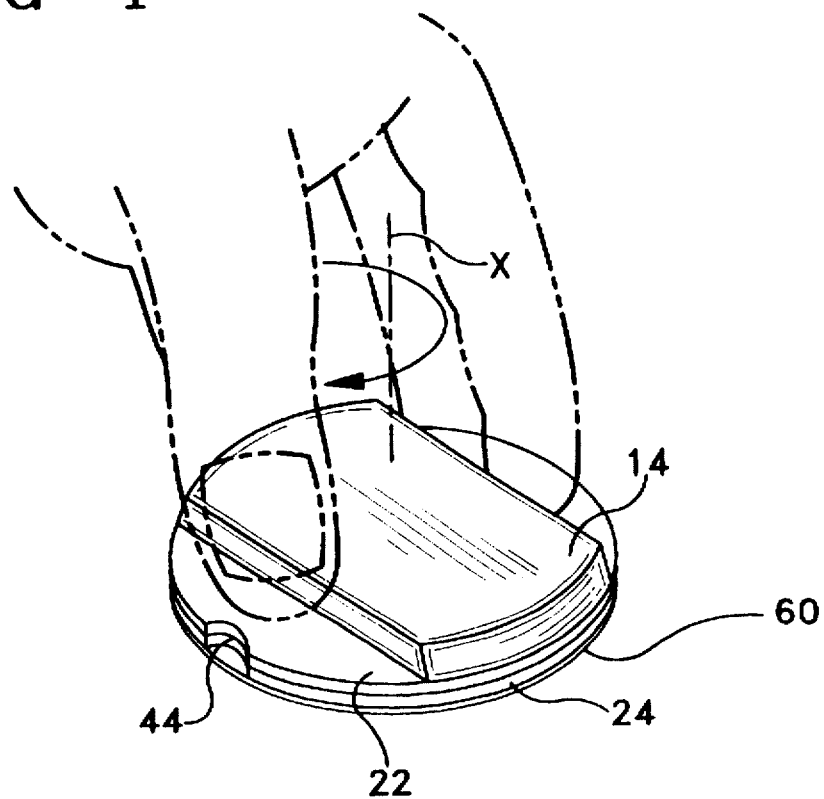
FIG. 4 is a perspective view of the iontophoretic drug delivery system illustrated in FIG. 3 with the controller attached to the patch and the system being manipulated to hydrate the drug, with FIG. 4A being an enlarged, cross-sectional view of the patch after rotation of the upper member relative to the lower member.
Figure 4A:
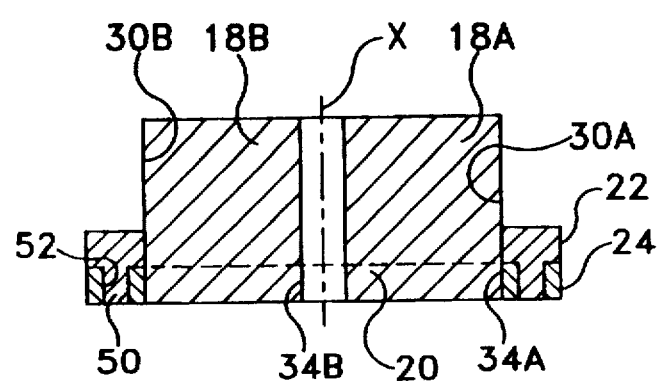

Also, as illustrated in FIG. 2, and in greater detail in FIG. 4A, the two supporting members 22, 24 are sealingly separated by a barrier, which can be manipulated to bring the drug reservoir 20 and the electrode reservoir into fluid conducting contact with one another. In this way, the drug contained in the drug reservoir can be stored or otherwise sealingly isolated from the electrode reservoirs 18A, 18B in the upper member 22, in a dry state or formulation in a matrix or on a supporting substrate for hydration prior to use.

In the preferred embodiment, the barrier is a foil or similar seal 40 attached around the periphery of the opening 34A by a suitable adhesive. In addition, the foil seal 40 includes an upper extending tab 42 which is preferably adhered or otherwise attached to the exposed surface of the upper member 22 so that the foil seal may easily peeled away from the opening by moving the upper member relative to the lower member.

Also, the patch 12 and the supporting members 22, 24, are preferably circular in shape, and rotate relative to one another about a central axis X. However, it should be appreciated that other shapes and configurations may be used. For example, a generally square shape or palm conforming shape may be utilized. In addition, to facilitate manipulation of the barrier and hydration of the drug reservoir, the upper member 22 and lower member 24 move about the central axis X relative to one another. In addition, to facilitate alignment of the supporting members 22, 24, at least one recess 44 is provided along their periphery edge. In this way, it is difficult to remove the release liner unless the patch has been activated.

Figure 3:
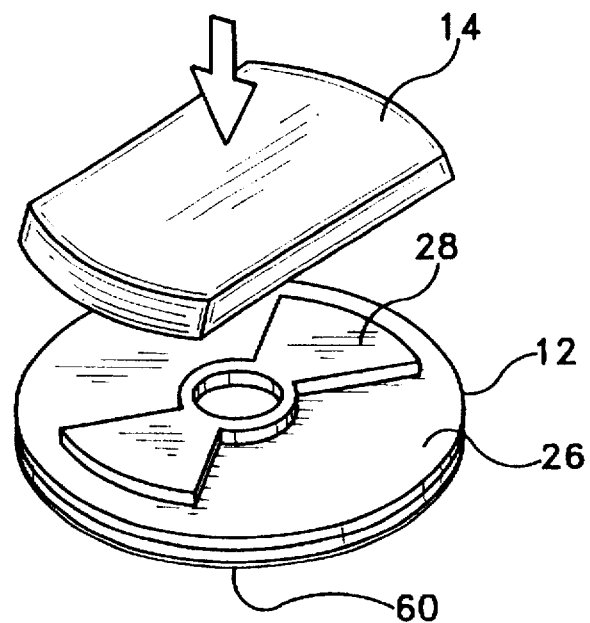
FIG. 3 is a perspective view of the iontophoretic drug delivery system illustrated in FIG. 2 showing the controller being attached to the patch, with FIG. 3A being an enlarged, cross-sectional view of the patch prior to rotation of the upper member relative to the lower member.
Figure 3A:
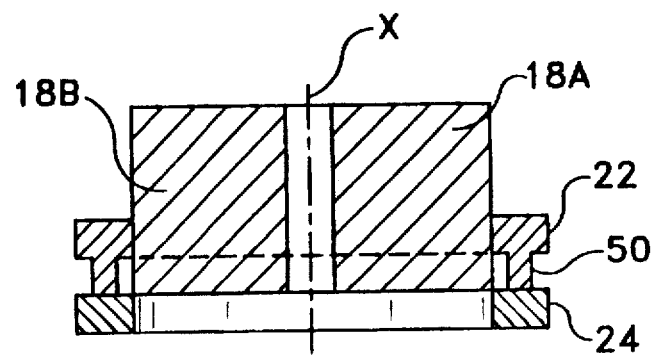

In the preferred embodiment illustrated in FIGS. 3A and 4A, the electrode reservoirs 18A, 18B extend outwardly from the compartments 30A, 30B. To insure sufficient separation of the lower member 24 and upper member 22, and a space or gap therebetween to accommodate the extending portions of the reservoirs, a spacer means 50 extends outwardly from one of the supporting members towards the other supporting member, with a corresponding, similarly shaped recess 52 formed in the other member. The gap between the members accommodates the extending portions of the electrode reservoirs. This is essential if the reservoirs are to extend sufficiently from the patch to come in electrically conducting contact with the skin of the patient when the device is placed thereon. Preferably, the spacer is in the form of a rail extending outwardly from the upper member 22, and the corresponding recess is formed in the lower member 24. Also, the recess 52 is positioned along the path of travel of the rail so that when the two members 22, 24 are rotated about the central axis X relative to one another, the rail 50 separates the members until the compartments 30A, 30B are positioned over the openings 34A, 34B. Once the rail 50 is positioned over the recess 52, with the compartments positioned over the openings, the rail drops into the recess and the members 22, 24 are brought into contract with one another. In this way, one of the electrode reservoirs 18A is brought into fluid conducting contact with the drug reservoir 20 contained in the opening 34A, and the other electrode reservoir 18B extends into the other opening 34B.

Also, as illustrated in FIGS. 2, 3, 4 and 5, a release liner 60 is attached to the exposed surface of the lower supporting member 24, which can be removed prior to application of the hydrated patch to the skin of the patient. In addition, it should be appreciated that in the alternative, or in combination therewith, the lower member 24 of the patch 12 may be removed to expose the reservoirs. In this way, the lower member 24 would act as a release liner to protect the reservoirs 18A, 18B, and upon removal of it, the exposed surface of the upper member 22, along with the extending portions of the reservoirs, could be brought into contact with the skin of the patient.

As illustrated in FIGS. 2, 3 and 4, the controller 14 is preferably reusable and releasably attachable to the patch 12. The particular controller is not essential to the present invention, but must include the microprocessor for controlling the supply of current delivered by the power source, and may include, for example, those disclosed in co-pending patent application Ser. No. 08/315,532, entitled "IONTOPHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER," Ser. No. 08/315,533 entitled "IONTOPHORESIS ASSEMBLY INCLUDING CLEANABLE ELECTRICAL CONTACTS," Ser. No. 08/315,372 entitled "APPARATUS AND METHOD FOR ENSURING COMPATIBILITY OF A REUSABLE IONTOPHORETIC CONTROLLER WITH AN IONTOPHORETIC PATCH," and Ser. No. 08/534,897, now abandoned, entitled "IONTOPHORETIC DRUG DELIVERY SYSTEM, INCLUDING REUSABLE DEVICE," and U.S. Pat. No. 5,498,235 (Flower), the disclosures of which are hereby incorporated by reference in their entirety. However, it is preferable that the controller 14 and the patch 12 be fastened by two interlocking members in the form of a female member and a corresponding male member extending from the top of the patch. Also, in the alternative, the controller can include outwardly extending fasteners with interlock with corresponding members in the raised portion 28 of the patch and which upon turn interlock to make an electrical connection between the patch and the controller as well as wipe and clean the electrical contacts. Also, the means for fastening the controller to the patch, including the corresponding male and female members, can be keyed to one another so as to insure that the right controller is used with the right patch.

The drug may include cell adhesive molecules, such as by way of example and not limitation, Glycoprotein IIb/IIIa receptor antagonists (GPIIb/IIIa) and other integrin receptor antagonists, such as, GPIc/IIa, $_{\alpha}B_3$ (Lefkovitz J., et al., "Platelet glycoprotein IIb/IIIa receptors in cardiovascular medicine." New Eng. J. Med. 332 (1995) 1553–9) which may be effective in the treatment of various disease states, e.g. restenosis, unstable angina, stroke, prevention of secondary myocardial infarction, etc. GPIIb/IIIa receptor antagonists bind to GPIIb/IIIa receptors on platelets to block fibrinogen binding and consequently inhibit platelet aggregation, as well as those disclosed in PCT Application No. WO 95/14683, entitled "NOVEL ISOXAZOLINE AND ISOXAZOLE FIBRINOGEN RECEPTOR ANTAGONISTS," the disclosure of which is hereby incorporated by reference in its entirety. These agents, therefore, have enormous potential for the treatment of various thromboembolic disorders. Also, the drug reservoir may include growth hormones in dry form, i.e., cotton or woven plastic thread, impregnated with the drug in a pre-determine amount per unit length. In addition, multiple layers of the Drug or various may be used.

Operation and Use

Figure 5:
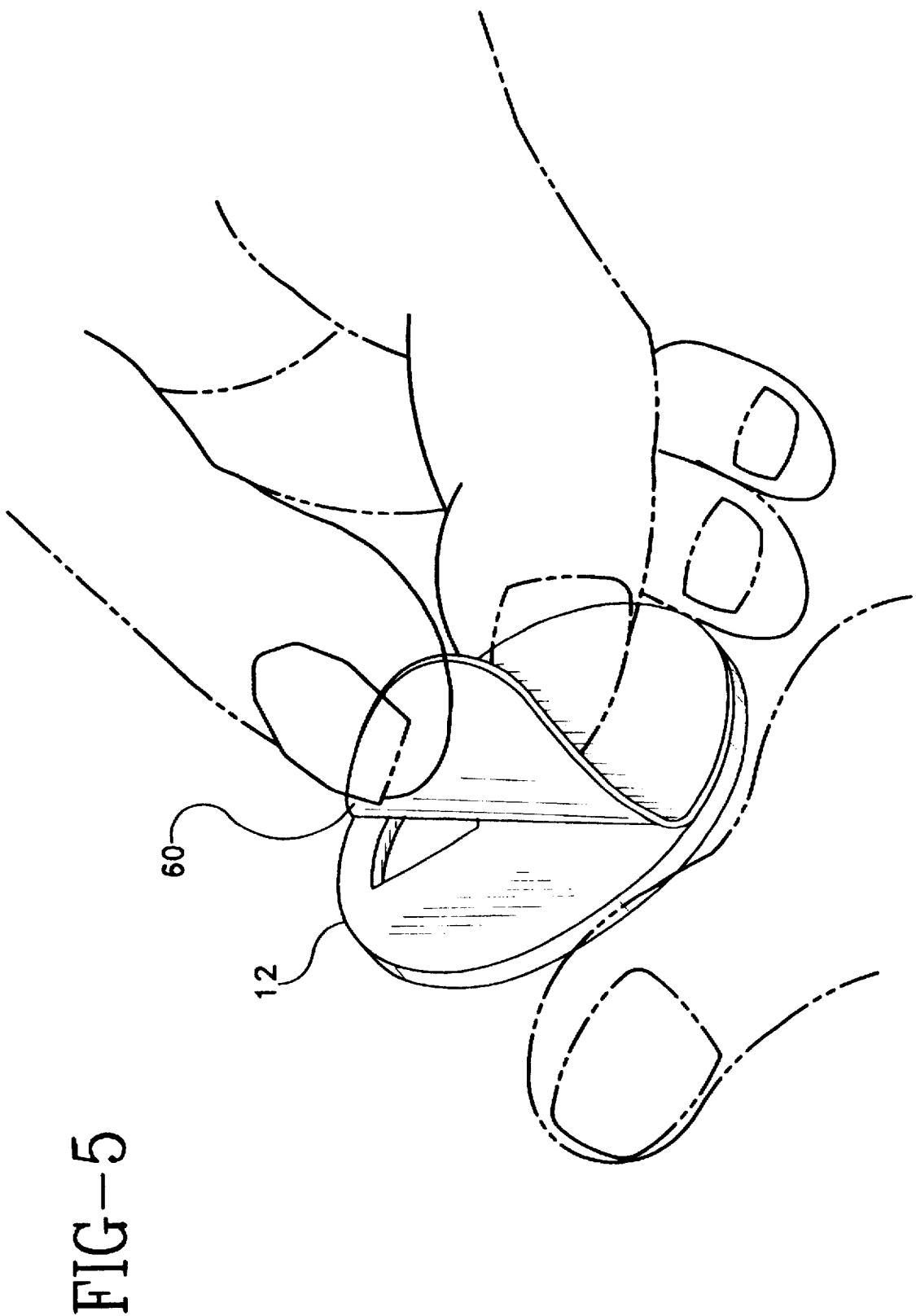
FIG. 5 is a perspective view of the iontophoretic drug delivery system illustrated in FIG. 4 showing the release liner being removed from the patch with the controller fastened thereto for attachment to the skin of the patient.

Having described the preferred embodiment of the iontophoretic drug delivery system 10, including the disposable patch 12 and reusable controller 14, of the present invention, its operation and use is described below in connection with FIGS. 3–5.

As illustrated in FIG. 3, the controller 14 is releasably fastened to the patch 12. Next, the controller 14 and the upper member 22 of the patch are rotated relative to the lower supporting member 24 to manipulate the barrier in the form of a foil seal 40 and bring the electrode reservoir 18A and drug reservoir 20 into contract with one another (FIG. 4). After waiting a sufficient period of time for hydration of the drug to be completed, the release liner 60 is removed from the patch for attachment of the system to the skin of the patient (FIG. 5). As previously explained, it should also be appreciated that the lower member 24 could act as a release liner and be removed form the patch for attachment.

Figure 1:
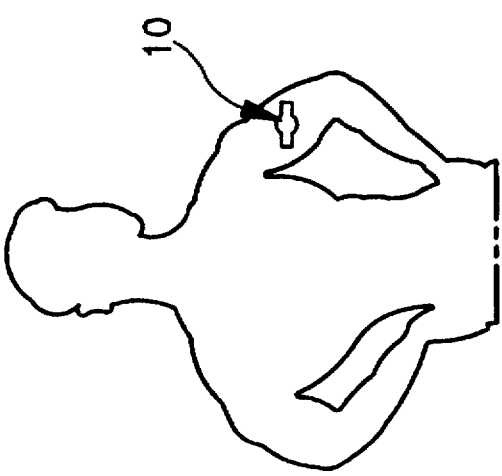

Because the tab 42 is secured to the upper member, the rotating action forces the foil seal 40 to be pulled from the lower supporting member 24 to expose the drug reservoir 20. Specifically, the pulling action causes the foil seal 40 to be drawn along with the upper member 22 as it is rotated to bring the electrode reservoirs in alignment with the openings 34A, 34B, particularly the opening 34A containing the drug reservoir 20 with the drug (active compound) to be delivered to the patient. Also, as the two members 22, 24 rotate relative to one another, the rail 50 is positioned above the corresponding recess 52 and drops therein to eliminate the space or gap separating the two members so as to bring them into contract with one another, as well as the electrode reservoir 18A and the drug reservoir 20 into fluid conducting contact with one another. In this way, the drug will be dissolved at the interface of the reservoirs, due to its solubility in an aqueous fluid and/or the drug reservoir is hydrated and adhered to the interface of the electrode reservoir 18A. Thereafter, the patch 12, with the controller 14 fastened thereto and the barrier manipulated, can be attached to the skin of the patient to deliver the drug (FIG. 1).

As is well known within the field, the device can be attached to a suitable area of the skin of the patient, with the drug containing patch in electrical conducting contact with the skin, and a voltage impressed across the electrodes of the electrode assembly to cause current to flow through the skin of the patient to drive the drug into the skin and the tissue to be absorbed by the body of the patient for the desired period of time. It should also be appreciated that the device of the present invention can be applied to other areas of the body such as mucus membranes depending upon the desired therapy and drugs to be delivered.

Active agent, drug, formulation, medication, medicament and active compound have been used herein to mean at least one pharmaceutical agent, such as therapeutic compounds, diagnostic agents, anesthetic agents and the like.

While the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

In addition, while the preferred embodiments of the present invention has been described so as to enable one skilled in the art to practice the system and method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A user activated iontophoretic device for use in delivering at least one medication through an applied area of a patient, such as the skin, mucus membrane and the like, comprising:

a first portion and a second portion, said first portion including an electrode assembly and an electrode reservoir and said second portion including a drug reservoir;

said electrode assembly including electrode means for driving a medication into the patient to be absorbed by the body of the patient;

said drug reservoir containing an active compound to be delivered to the applied area of the patient; and barrier means for sealing said drug reservoir in said second portion and including a foil seal having a tab, with the foil seal being adhered along the peripheral edge of the drug reservoir and the tab being adhered to the first portion so that movement of said first portion relative to said second portion manipulates said barrier means and brings the electrode reservoir and the drug reservoir into fluid conducting contact with one another, whereby said reservoirs are sealingly separated from one another with the active compound contained in the drug reservoir being isolated from the electrode reservoir in the first portion prior to activation so that upon alignment of said reservoirs and manipulation of said barrier means, the electrode reservoir and the drug reservoir are brought into fluid conducting contact with one another so that said drug is dissolved in an aqueous solution contained in said electrode reservoir.

2. The user activated iontophoretic device as defined in claim 1, wherein said active compound is initially in a dry form, separated from the electrode reservoir with the barrier means sealing said drug reservoir in said second portion.

3. The user activated iontophoretic device as defined in claim 1, wherein the active compound is in a dry form and homogeneously distributed in a carrier material so that the active compound may be kept in a dry form, separated from the electrode reservoir.

4. The user activated iontophoretic device as defined in claim 1, wherein the electrode reservoir includes an electrolyte in the form of an electrically conductive gel.

5. The user activated iontophoretic device as defined in claim 1, wherein the active compound is selected from the group consisting of cell adhesion molecules, GPIIb/IIIa receptor antagonists for the treatment of various throinboembolic disorders.

6. The user activated iontophoretic device as defined in claim 1, wherein the adhering force adhering said tab to said first portion is greater than the adhering force adhering said foil seal to said second portion.

7. The user activated iontophoretic device as defined in claim 1, wherein said first portion includes a compartment for at least containing the electrode reservoir and said second portion includes a compartment for containing said drug reservoir with the compartments sealingly separated by said barrier means so that said active compound is otherwise isolated from the electrode reservoir and the device may be activated by manipulating said barrier means to bring the electrode reservoir and the drug reservoir into fluid conducting contact with one another.

8. The user activated iontophoretic device as defined in claim 1, further comprising at least one spacer for separating said first portion before activation and said second portion, with said spacer upon activation extending outwardly from either said first portion or said second portion and a corresponding recess formed in the other portion for accommodating said spacer.

9. A user activated iontophoretic device for use in delivering at least one medication through an applied area of a patient such as the skin, mucus membrane and the like, comprising:

a first portion and a second portion, said first portion including an electrode assembly and an electrode reservoir and said second portion including a drug reservoir;

at least one spacer for separating said first portion before activation and said second portion, with said spacer extending outwardly from either said first portion or said second portion and a corresponding recess formed in the other portion for accommodating said spacer upon activation;

said electrode assembly including electrode means for driving a medication into the patient to be absorbed by the body of the patient;

said drug reservoir containing an active compound to be delivered to the applied area of the patient; and barrier means for sealing said drug reservoir in said second portion whereby said reservoirs are sealingly separated from one another with the active compound contained in the drug reservoir being isolated from the electrode reservoir in the first portion prior to activation so that upon alignment of said reservoirs and manipulation of said barrier means the electrode reservoir and the drug reservoir are brought into fluid conducting contact with one another so that said drug is dissolved in an aqueous solution contained in said electrode reservoir.

10. The user activated iontophoretic device as defined in claim 9, wherein said barrier means includes a foil seal having a tab, with the foil seal being adhered along the peripheral edge of the drug reservoir and the tab being adhered to the first portion so that movement of said first portion relative to said second portion manipulates said barrier means and brings the electrode reservoir and the drug reservoir into fluid conducting contact with one another.

11. The user activated iontophoretic device as defined in claim 10, wherein the adhering force adhering said tab to said first portion is greater than the adhering force adhering said foil seal to said second portion.

12. The user activated iontophoretic device as defined in claim 9, wherein said first portion includes a compartment for at least containing the electrode reservoir and said second portion includes a compartment for containing said drug reservoir with the compartments sealingly separated by said barrier means so that said active compound is otherwise isolated from the electrode reservoir and the device may be activated by manipulating said barrier means to bring the electrode reservoir and the drug reservoir into fluid conducting contact with one another.

13. The user activated iontophoretic device as defined in claim 9, wherein the electrode reservoir includes an electrolyte in the form of an electrically conductive gel.

14. The user activated iontophoretic device as defined in claim 9, wherein the active compound is selected from the group consisting of cell adhesion molecules, GPIIb/IIIa receptor antagonists for the treatment of various thromboembolic disorders.

15. The user activated iontophoretic device as defined in claim 9, wherein said active compound is initially in a dry form, separated from the electrode reservoir with the barrier means sealing said drug reservoir in said second portion.

16. A method of iontophoretically delivering at least one medication through an applied area of a patient such as the skin, mucus membrane or the like, comprising the steps of:

releasably fastening a controller to a disposable patch, with said patch including an upper portion and a lower portion;

rotating said upper portion about a central axis relative to said lower portion;

manipulating a barrier means sealingly separating at least one electrode reservoir contained in said upper portion and a drug reservoir contained in said lower portion, with said drug reservoir containing an active compound to be delivered to the patient and said active compound initially being in a dry state;

bringing the electrode reservoir of the upper portion into fluid conducting contact with the drug reservoir of the lower portion to at least partially hydrate one of said reservoirs and to form a combined reservoir, with the combined reservoir to be applied to an area of the patient to be treated; and causing current to flow through the device into the applied area to drive the medication into the body of the patient.

17. The method of iontophoretically delivering at least one medication as defined in claim 16, wherein the step of bringing the two portions into contact with one another includes manipulating a seal at least partially releasably adhered to the lower portion.

18. The method of iontophoretically delivering at least one medication as defined in claim 16, further comprising the step of removing a release liner from said lower portion to expose said reservoirs for application to the skin of the patient.

19. A method of iontophoretically delivering at least one medication as defined in claim 16, wherein said step of bring said electrode reservoir and said drug reservoir into contact with one another includes hydrating said drug reservoir.

20. A method of iontophoretically delivering at least one medication as defined in claim 16, wherein during said step of said electrode reservoir and said drug reservoirs into fluid conducting contact the drug contained in said drug reservoir is dissolved into said electrode reservoir.

* * * * *